(12) United States Patent
Boege et al.

(10) Patent No.: US 8,492,138 B2
(45) Date of Patent: *Jul. 23, 2013

(54) OPTICAL INSTRUMENT INCLUDING EXCITATION SOURCE

(75) Inventors: Steven J. Boege, San Mateo, CA (US); Howard G. King, Berkeley, CA (US); Eugene F. Young, Marietta, GA (US); Johannes P. Sluis, Redwood City, CA (US); Mark F. Oldham, Emerald Hills, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/611,462

(22) Filed: Sep. 12, 2012

(65) Prior Publication Data
US 2013/0011848 A1  Jan. 10, 2013

Related U.S. Application Data

(63) Continuation of application No. 12/217,410, filed on Jul. 3, 2008, which is a continuation of application No. 10/440,920, filed on May 19, 2003, now Pat. No. 7,410,793, and a continuation-in-part of application No. 10/216,620, filed on Aug. 9, 2002, now Pat. No. 7,008,789, which is a continuation of application No. 09/700,536, filed as application No. PCT/US99/11088 on May 17, 1999, now Pat. No. 6,818,437.

(60) Provisional application No. 60/381,671, filed on May 17, 2002, provisional application No. 60/409,152, filed on Sep. 9, 2002, provisional application No. 60/450,734, filed on Feb. 28, 2003.

(51) Int. Cl.
*C12M 1/34* (2006.01)
*C12M 3/00* (2006.01)

(52) U.S. Cl.
USPC ..... 435/288.7; 435/808; 435/809; 250/459.1; 250/461.1; 250/461.2; 250/462.1; 250/483.1

(58) Field of Classification Search
USPC ......... 435/283.1, 288.7, 809, 808; 250/459.1, 250/461.1, 461.2, 462.1, 483.1
See application file for complete search history.

(56) References Cited

U.S. PATENT DOCUMENTS

| | | | |
|---|---|---|---|
| 3,973,129 A | 8/1976 | Blumberg et al. | |
| 4,284,897 A | 8/1981 | Sawamura et al. | |

(Continued)

FOREIGN PATENT DOCUMENTS

| | | |
|---|---|---|
| EP | 0065409 | 11/1982 |
| EP | 0622455 | 11/1994 |

(Continued)

OTHER PUBLICATIONS 03738941.8, "Office Action Mailed Sep. 1, 2010", 7 pgs.

(Continued)

*Primary Examiner* — Nathan Bowers

(57) ABSTRACT

An optical instrument is provided for simultaneously illuminating two or more spaced-apart reaction regions with excitation beams generated by a light source. The light source can include an area light array of light emitting diodes, one or more solid state lasers, one or more micro-wire lasers, or a combination thereof. According to various embodiments, a Fresnel lens can be disposed along a beam bath between the light source and the reaction regions. Methods of analysis using the optical instrument are also provided.

29 Claims, 8 Drawing Sheets

U.S. PATENT DOCUMENTS

| | | | |
|---|---|---|---|
| 4,626,684 | A | 12/1986 | Landa |
| 4,643,877 | A | 2/1987 | Opitz |
| 4,673,289 | A | 6/1987 | Gaucher |
| 4,683,202 | A | 7/1987 | Mullis |
| 5,073,029 | A | 12/1991 | Eberly et al. |
| 5,091,652 | A | 2/1992 | Mathies et al. |
| 5,169,601 | A | 12/1992 | Ohta et al. |
| 5,215,883 | A | 6/1993 | Chu |
| 5,243,540 | A | 9/1993 | Van Albert et al. |
| 5,256,880 | A | 10/1993 | Loree et al. |
| 5,315,375 | A | 5/1994 | Allen |
| 5,355,215 | A | 10/1994 | Schroeder et al. |
| 5,371,016 | A | 12/1994 | Berndt |
| 5,383,023 | A | 1/1995 | Walleczek |
| 5,389,544 | A | 2/1995 | Sugata et al. |
| 5,397,709 | A | 3/1995 | Berndt |
| 5,475,610 | A | 12/1995 | Atwood et al. |
| 5,547,849 | A | 8/1996 | Baer et al. |
| 5,567,947 | A | 10/1996 | Kebabian |
| 5,595,708 | A | 1/1997 | Berndt |
| 5,656,493 | A | 8/1997 | Mullis et al. |
| 5,672,880 | A | 9/1997 | Kain |
| 5,736,333 | A | 4/1998 | Livak et al. |
| 5,759,781 | A | 6/1998 | Ward et al. |
| 5,766,889 | A | 6/1998 | Atwood |
| 5,779,978 | A | 7/1998 | Hartmann et al. |
| 5,792,610 | A | 8/1998 | Witney et al. |
| 5,846,842 | A | 12/1998 | Herron et al. |
| 5,854,684 | A | 12/1998 | Stabile et al. |
| 5,863,502 | A | 1/1999 | Southgate |
| 5,891,656 | A | 4/1999 | Zarling et al. |
| 5,926,271 | A | 7/1999 | Couderc et al. |
| 5,928,907 | A | 7/1999 | Woudenberg et al. |
| 5,943,129 | A | 8/1999 | Hoyt et al. |
| 6,040,940 | A | 3/2000 | Kawasaki |
| 6,057,114 | A | 5/2000 | Akong et al. |
| 6,096,272 | A | 8/2000 | Clark et al. |
| 6,121,603 | A | 9/2000 | Hang et al. |
| 6,132,578 | A | 10/2000 | Kambara et al. |
| 6,184,535 | B1 | 2/2001 | Kashima et al. |
| 6,197,575 | B1 | 3/2001 | Griffith et al. |
| 6,287,871 | B1 | 9/2001 | Herron et al. |
| 6,309,601 | B1 | 10/2001 | Juncosa et al. |
| 6,331,438 | B1 | 12/2001 | Aylott et al. |
| 6,331,441 | B1 | 12/2001 | Batch |
| 6,337,740 | B1 | 1/2002 | Parce |
| 6,352,672 | B1 | 3/2002 | Mabile |
| 6,355,934 | B1 | 3/2002 | Osgood et al. |
| 6,364,516 | B1 | 4/2002 | Li et al. |
| 6,388,788 | B1 | 5/2002 | Harris |
| 6,399,936 | B1 | 6/2002 | Hang et al. |
| 6,411,835 | B1 | 6/2002 | Modell et al. |
| 6,455,861 | B1 * | 9/2002 | Hoyt ............................ 250/458.1 |
| 6,529,275 | B2 | 3/2003 | Amirkhanian et al. |
| 6,534,011 | B1 | 3/2003 | Karthe et al. |
| 6,558,624 | B1 | 5/2003 | Lemmon et al. |
| 6,597,000 | B2 | 7/2003 | Stern |
| 6,603,537 | B1 | 8/2003 | Dietz et al. |
| 6,743,581 | B1 | 6/2004 | Vo-Dinh |
| 6,930,314 | B2 | 8/2005 | Jackson et al. |
| 6,958,464 | B2 | 10/2005 | Olszak et al. |
| 6,979,567 | B2 | 12/2005 | Herron et al. |
| 7,635,588 | B2 | 12/2009 | King |
| 2001/0033374 | A1 | 10/2001 | Hoyt |
| 2002/0024026 | A1 | 2/2002 | Kaushikkar |
| 2002/0055178 | A1 | 5/2002 | Wardlaw |
| 2002/0060791 | A1 | 5/2002 | Stumbo et al. |
| 2002/0109100 | A1 | 8/2002 | Jackson et al. |
| 2002/0146688 | A1 | 10/2002 | Kinjo |
| 2002/0160535 | A1 | 10/2002 | Herron et al. |
| 2002/0185610 | A1 | 12/2002 | Stern |
| 2003/0160182 | A1 | 8/2003 | Petrich et al. |
| 2003/0230728 | A1 | 12/2003 | Dai et al. |
| 2010/0216143 | A1 | 8/2010 | King |

FOREIGN PATENT DOCUMENTS

| | | |
|---|---|---|
| EP | 0640828 A1 | 3/1995 |
| EP | 0987539 | 3/2000 |
| EP | 0640828 B1 | 5/2000 |
| EP | 1124128 | 8/2001 |
| JP | 07120392 | 5/1995 |
| JP | 07120393 | 5/1995 |
| JP | 07174701 | 7/1995 |
| JP | 09281078 | 10/1997 |
| WO | WO-9723649 | 7/1997 |
| WO | WO-97/46707 | 12/1997 |
| WO | WO-98/57151 | 12/1998 |
| WO | WO-99/08096 | 2/1999 |
| WO | WO-99/60381 | 11/1999 |
| WO | WO-0013017 | 3/2000 |
| WO | WO-00/31518 | 6/2000 |
| WO | WO-00/58715 | 10/2000 |
| WO | WO-01/03507 | 5/2001 |
| WO | WO-01/69211 | 9/2001 |
| WO | WO-01/77648 | 10/2001 |
| WO | WO-01/84463 | 11/2001 |
| WO | WO-01/96837 | 12/2001 |
| WO | WO-03/021212 | 3/2003 |
| WO | WO-03/023829 | 3/2003 |

OTHER PUBLICATIONS 03738941.8, "Office Action mailed on Feb. 8, 2010", 6 pgs.
03738941.8, "Response to Feb. 8, 2010 Office Action mailed", Filed on Jun. 2, 2010, 3 pgs.
03738941.8, "Response to Sep. 1, 2010 Office Action mailed", Filed on Jan. 10, 2011, 3 pgs.
03753099.5, "European Search Report mailed Nov. 5, 2009", 3 pgs.
037530995, "Office Action Mailed Feb. 11, 2010", 5 pgs.
037530995, "Response to Feb. 11, 2010 Office Action Mailed", Filed on Aug. 23, 2010, 10 pgs.
U.S. Appl. No. 10/440,852, "Notice of Allowance mailed on Aug. 7, 2009", 6 pgs.
U.S. Appl. No. 12/217,410, "Office Action Mailed Nov. 10, 2010", 15 pgs.
U.S. Appl. No. 12/217,410, "Office Action Mailed Apr. 2, 2010", 20 pgs.
U.S. Appl. No. 12/642,009, "Office Action Mailed Jun. 17, 2011", 22 pgs.
U.S. Appl. No. 12/642,009, "Office Action Mailed Nov. 17, 2010", 21 pgs.
U.S. Appl. No. 12/642,009, "Response to Nov. 17, 2010 Office Action Mailed", Filed on Apr. 18, 2011, 10.
Ealing, "Product catalog", 18 pgs.
EP037389418, "European Search Report mailed Nov. 3, 2009", 4 pgs.
EP11193359, "European Search Report mailed Mar. 27, 2012", 9 pgs.
H W Sands Corporation, "OLED Emitters Selected by Color Emission", http://www.hwsands.com|productlists/oled/oled_emitters_color_emission.htm, Jan. 10, 2003, 5 pgs.
Hebner, T. R. et al., "Local Tuning of Organic Light-Emitting Diode Color by Dye Droplet Application American Institute of Physics.", *Applied Physics, Letters 73*, 1998, 1775-1777.
Higuchi, et al., "Real-Time Monitoring of DNA Amplification Reactions", *Kinetic PCR Analysis, Bio Technology*, vol. II, 1993, pp. 1026-1030.
Higuchi, R. et al., "Kinetic PCR Analysis: Real-Time Monitoring of DNA Amplification Reactions", *BioTechnology*, vol. 11, Sep. 1993, 1026-1030.
Lasercomponents.Com App. Note, "http://www.lasercomponents.com/de/?embedded=1&file=fileadmin/user_upload/home|Datasheets/omega/application-notes-filters.pdf&no_cache=1".
Omega, "Product catalog", 37 pages.
PCT/US03/15941, International Search Report, mailed Dec. 2, 2003, 4 pgs.
PCT/US99/011088, PCT/US99/011088 International Search Report mailed Sep. 15, 1999, 3 pgs.

Qiu, et al., "Room Temperature Ultraviolet Emission From an Organic Light-Emitting Diode", *American Institute of Physics*, Jul. 25, 2001, 2276-2278.

Ririe, et al., "Product Differentiation by Analysis of DNA Melting Curves During the Polymerase Chain Reaction", *Analytical Biochemistry*, vol. 245, 1997, 154-160.

Teresko, "Winning Technologies: Organic Light Emitting Diode", *Industry Week*, Dec. 11, 2000, 3 pgs.

Tollefsrud, "Organic Light Emitting Diode", http://komar.cs.stthornas.edulqm425/01s|Tollefsrud2.htm, Tollefsrud, Electronic Paper, Jan. 10, 2003, 5 pgs.

Wittwer, C.T. et al., "The LightCycler™: A Microvolume Multisample Fluorimeter with Rapid Temperature Control", *BioTechniques*, vol. 22 (1), Jan. 1997, 176-181.

\* cited by examiner

US 8,492,138 B2

OPTICAL INSTRUMENT INCLUDING EXCITATION SOURCE

CROSS-REFERENCE TO RELATED APPLICATIONS

This application is a continuation of U.S. patent application Ser. No. 12/217,410, filed Jul. 3, 2008, which is a continuation of U.S. application Ser. No. 10/440,920, filed May 19, 2003, now U.S. Pat. No. 7,410,793, which claims the benefit of U.S. Provisional Patent Application No. 60/381,671, filed May 17, 2002, U.S. Provisional Patent Application No. 60/409,152, filed Sep. 9, 2002, and U.S. Provisional Patent Application No. 60/450,734, filed Feb. 28, 2003, and is a continuation-in-part of U.S. patent application Ser. No. 10/216,620, filed Aug. 9, 2002, now U.S. Pat. No. 7,008,789, which is a continuation of U.S. patent application Ser. No. 09/700,536, filed Nov. 29, 2001, now U.S. Pat. No. 6,818,437, which is a National Stage of International Application No. PCT/US99/11088, filed May 17, 1999, which published as publication number WO 99/60381. Cross-reference is made to co-pending U.S. patent application Ser. No. 10/440,852, and to U.S. patent application Ser. No. 10/440,719, both filed May 19, 2003. All the above mentioned Patents, Patent Applications, and publications are herein incorporated by reference in their entirety.

FIELD

The present invention relates to instrumentation for detecting and measuring fluorescence, and to methods of using the instrumentation.

BACKGROUND

Fluorometers are described, for example, in International Publications No. WO 01/35079 and WO 99/60381, both of which are incorporated herein in their entireties by reference.

For various applications, an inexpensive optical instrument including a low heat-generating light source that uses minimal power is desirable. For various purposes, an inexpensive optical instrument including an LED excitation source capable of simultaneously illuminating one or more sample containers is desirable.

SUMMARY

According to various embodiments, an instrument for use in the analysis of one or more analytes is provided. The instrument can include a plurality of spaced-apart reaction regions, an excitation source adapted to simultaneously illuminate one or more of the spaced-apart reaction regions, and, optionally, a Fresnel lens disposed along a beam path between the excitation source and the spaced-apart reaction regions. The excitation source can comprise an array of light sources.

According to various embodiments, an optical system can include a Fresnel lens that focuses excitation beams radiated from a light source to simultaneously illuminate one or more of a plurality of spaced-apart reaction regions, for example, one or more wells of a multi-well microtiter plate.

According to various embodiments, methods are provided for simultaneously illuminating one or more of a plurality of spaced-apart reaction regions with excitation beams generated from a light source comprising an array of light sources.

Additional embodiments are set forth in part in the description that follows, and in part will be apparent from the description, or may be learned by practice of the various embodiments.

BRIEF DESCRIPTION OF THE DRAWINGS

FIGS. 7a-7c are schematic diagrams of a modular light source, according to various embodiments, wherein FIG. 7a is a light source module, FIG. 7b is a light source lens array capable of mounting on the light source module and including two light source lenses, and FIG. 7c is a light source lens array capable of mounting on the light source module and including four light source lenses;

It is to be understood that both the foregoing general description and the following detailed description are exemplary and explanatory only and are intended to provide a further explanation of the various embodiments of the present invention.

DESCRIPTION OF VARIOUS EMBODIMENTS

Various embodiments described herein provide an instrument for use in the analysis of one or more analytes. According to various embodiments, the instrument includes a plurality of spaced-apart reaction regions, a light source adapted to simultaneously illuminate one or more of the reaction regions with excitation radiation, and optionally a Fresnel lens disposed along a beam path between the light source and the reaction regions. An exemplary embodiment is shown in FIG. 1.

Figure 1:
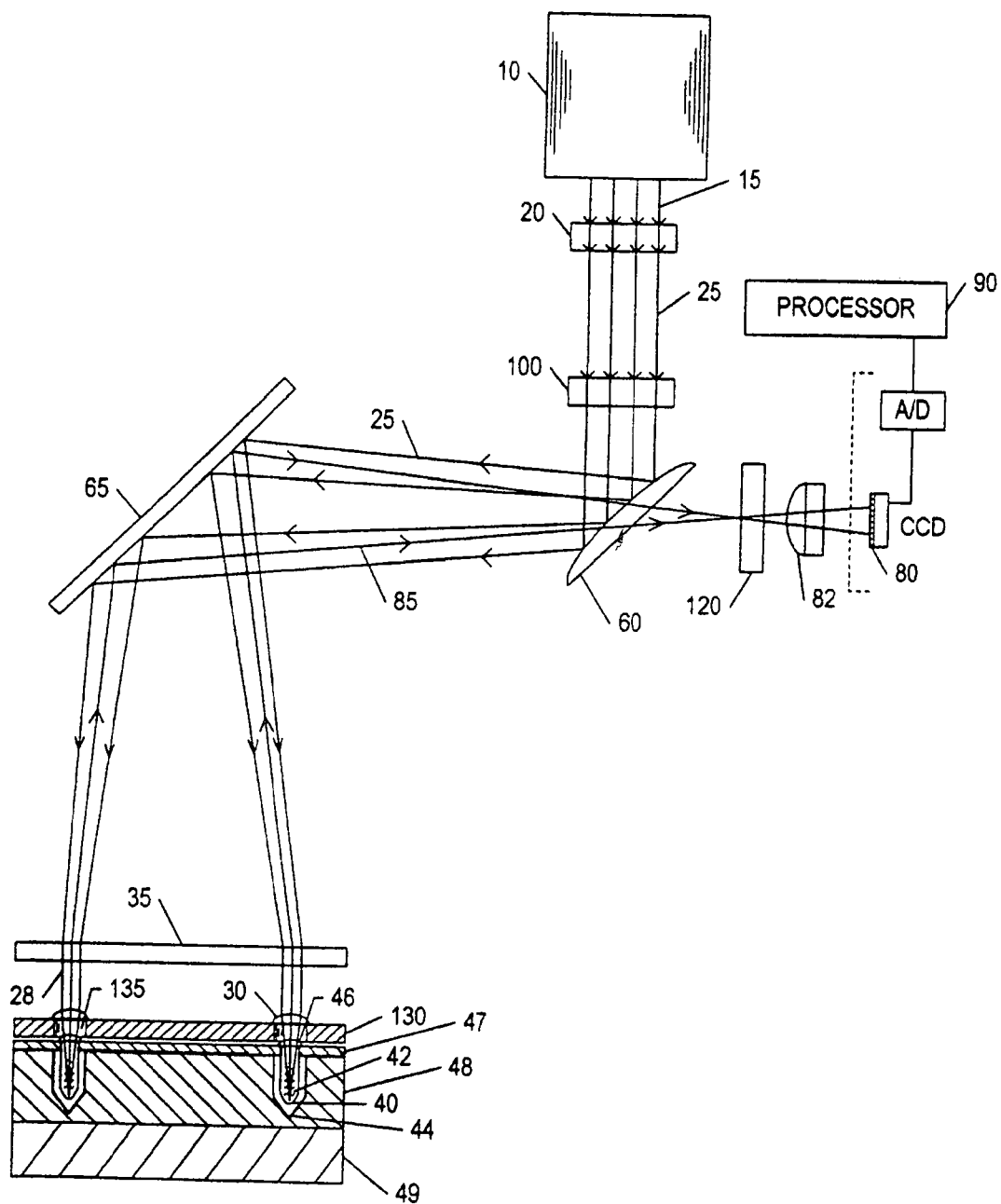
FIG. 1 is a schematic diagram of an optical instrument and an optical pathway generated by the instrument according to various embodiments.

FIG. 1 shows an exemplary instrument according to various embodiments that can include a reaction region holding assembly 48, for example, a thermal cycler block, including wells 44 for holding respective reaction regions 40, for example, vials, spaced apart from one another. The reaction regions contain respective samples 42. The samples can be, for example, respective suspensions of ingredients for polymerase chain reaction (PCR). If the reaction region holding assembly 48 is a thermal cycler block, the assembly 48 can include a thermal cycle controller 49 for cycling the temperature of the block through a temperature program.

Each reaction region 40 can include, for example, any chamber, vessel, container, sample well, capsule, vial, sample array, centrifuge tube, or other containing, restraining, retaining, or confining device, without limitation, that is capable of retaining one or more samples for fluorometric analysis or illumination thereof. The reaction regions 40 can be fixed, secured, mounted, or otherwise attached or connected to, separate from, or integral with, the reaction region holding assembly 48. The assembly 48 can be attached or connected to, or placed on, a surface of a substrate or a holder and positioned to enable one or more of the reaction regions to be illuminated by a light source. The holding assembly can be, for example, a purification tray, microtiter tray, multiwell tray, sample array, micro-well array or like device for holding multiple samples.

The samples 42 to be analyzed can include aqueous suspensions of sample materials, for example, that might include a "seed" sample of a target nucleic acid sequence, selected primers, nucleic acids, enzymes, buffers, and other chemicals conventionally used for PCR, for an isothermal reaction or another DNA amplification method well known in the art.

The reaction regions 40 can be heated and cooled in a predetermined cycle by electric heaters, liquid or air coolants, or a combination of these, or by other methods to achieve thermal cycling. The reaction regions 40 can be cycled between two temperature phases so as to affect PCR, for example.

Spaced-apart reaction regions 40, for example, conical or cylindrical vials, can be separate from each other, or can be integrally formed in a unitary tray, for example, a plastic tray. The reaction region holding assembly 48 can hold a plurality of vials, for example, 96, in an array, such as an array of 12 by 8 vials. According to various embodiments, the vials or reaction regions can be removed from the reaction region holding assembly 48 for preparation and/or sample loading. According to various embodiments, a plastic unitary cover, such as a cover including caps 46, can be provided to seal the vials.

The caps 46 can rest on, attach to, or seal tightly with the reaction regions 40 to prevent contamination and evaporative loss of the samples 42 in the reaction regions 40. Other methods and instruments can be used for this function, such as disposing oil such as mineral oil on the sample surface, in which case caps may not be needed. If used, caps 46 can be transparent to light utilized in the instrument. The caps 46 can be convex, for example, facing upwardly. According to various embodiments and as shown in FIG. 1, convex, upwardly-facing caps 46 can function as reaction region lenses to focus respective bundles 28 of excitation beams into a sample 42 in a respective reaction region 40.

According to various embodiments, each cap 46 can fit snuggly on or in each respective vial 40 such that the cap 46 when fit into or onto vial 40 can support the weight of vial 40 suspended from the cap 46. According to various embodiments wherein vial 40 is suspended from cap 46, the cap can have a mushroom-like shape, having a convex top and a narrower base protruding below the top such that the narrower base can fit snuggly into vial 40. The cap 46 supporting the vial 40 can rest on a platform 47, as shown in FIG. 1, wherein the platform has through holes for passage of vials 40 through the platform such that caps 46 rest on platform 47 while vials 40 are suspended from caps 46 and extend through platform 47. According to various embodiments, a plurality of caps 46 can be formed as a single sheet such that the sheet can be laid over a plurality of reaction regions such as vials 40. A plurality of caps 46 can be formed as a single heat shield cover sheet.

According to various embodiments, a monitoring instrument can be mounted over the reaction region holding assembly 48 containing the reaction regions 40. The instrument can be removable or can swing away for access to the reaction regions 40.

As shown in FIG. 1, for example, the instrument can include a platen 130 that rests over the caps 46 or, if no caps are used, that rests directly over the reaction regions 40. The platen 130 can be aluminum and can include an array of holes 135 aligned with reaction regions 40, with each hole having a diameter that is about the same as the top diameter of the reaction region. If caps 46 are used, the platen 130 can have its temperature maintained by a film heater or other instrument to prevent condensation from forming under the caps 46. The heating of the platen, however, should not interfere with the reaction, such as DNA replication, in the reaction regions 40. An exemplary method to prevent condensation is to maintain the platen 130 at a slightly higher temperature than the highest sample temperature that the reaction region holding assembly 48 reaches.

According to various embodiments and as depicted in FIG. 1, a focusing lens such as a reaction region lens 30 can be positioned above each of reaction regions 40 so that a focal point of the focusing lens is approximately centered in a respective sample 42 in a respective reaction region 40. A focusing lens 35, for example, an objective lens or a Fresnel lens, can be placed above reaction region lens 30 to provide, for example, a telecentric optical system. The terms "focusing lens" and "reaction region lens" used throughout this disclosure can be interchangeable in that a reaction region lens, a focusing lens, or both can be present according to various embodiments. Each focusing lens 35 and each reaction lens 30 can include two or more lenses that can together affect a desired focus, thus the word "lens" herein includes such multiplicities. A convex, upwardly-facing cap of a reaction region can function, for example, as a reaction region lens. According to various embodiments, a Fresnel lens as a focusing lens 35 and a reaction region lens 30 can be present in the instrument. A neutral density pattern (not shown) to correct inconsistencies in illumination and imaging can be mounted on or in proximity to the focusing lens or reaction region lens, for example, to attenuate light in the center of the image field.

A fluorescent marker or dye in a sample in a reaction region can emit light at an emission frequency when excited by an excitation beam of the appropriate wavelength. The emitted light can be passed as emission beam 85 to a detector 80. According to various embodiments, emission beam 85 can pass through a reaction region lens 30 and/or focusing lens 35, such as Fresnel lens, to a detector 80. A fold mirror 65 can be optionally mounted at a 45° angle, or any other suitable angle, for convenient packaging. The fold mirror 65 can be omitted, or other such folding optics can be used instead or in addition to the fold mirror. According to various embodiments, emission beam 85 can be reflected by fold mirror 65 toward a filter 60, such as a long pass filter or beam splitter. Filter 60 can pass or reflect an emission beam 85 to detector 80. According to various embodiments, filter 60 can include a curved surface, as shown in FIG. 1.

One or more of reaction region lens 30, focusing lens 35, and cap 46 can provide a primary focusing system for focusing the excitation beams into reaction region 40 and/or for focusing emission beams 85 toward a detector 80. According to various embodiments, focusing lens 35 can be omitted so that the focusing system includes reaction region lens 30, or vice versa. According to various embodiments, a plurality of reaction region lenses can form a reaction region lens array, wherein each reaction region lens can correspond to a separate reaction region. A lens array can be incorporated into a Fresnel lens. A single structure that has a plurality of optical elements built into the structure can also be used. The reaction region lens can be disposed between the Fresnel lens and the reaction region such that each bundle of excitation beams from the light source passes through the Fresnel lens and impinges on a respective reaction region lens, and can be focused on a sample in a respective reaction region. According to various embodiments, one or more of the focusing lens 35, the reaction region lens 30, and the cap 46 can focus the emission beams 85 on a detector 80.

According to various embodiments and as depicted in FIG. 1, a filter 60, such as a long pass filter, can be disposed to receive excitation beams 15 from the light source 10. According to various embodiments and as shown in FIG. 1, filter 60 can be disposed to receive excitation beams 25 from excitation filter 100. The filter 60 can be a dichroic reflector such that, when positioned at an angle, such as 45°, the filter reflects excitation beams to illuminate one or more of the reaction regions 40 with excitation beams 25 that can cause one or more dye in each respective sample to fluoresce at an emission frequency to produce an emission beam. According to various embodiments, the filter 60 can pass light having the emission frequency. Such a filter can utilize optical interference layers to provide a desired frequency response.

According to various embodiments as shown in FIG. 1, and with any of the light sources described herein, filter 60 can be positioned so that filter 60 can reflect the excitation beams to fold mirror 65. The excitation beams 15 can be reflected from the filter 60 as excitation beams 25 having the excitation frequency. Excitation beams 25 are reflected off the fold mirror 65 towards the respective reaction regions 40. The reflected excitation beams can be focused by Fresnel lens 35 as separated beams 28 which pass through the reaction region lens 30 and are focused into the center of the samples 42 of the respective reaction regions 40.

According to various embodiments, filter 60 can pass excitation beams 15 as excitation beams 25 and reflect emission beams 85. According to various embodiments, angles other than 45° can be used if they are more suitable for the filter 60. Although filter 60 can split the optical paths of the excitation beams 25 from the emission beams 85, other variations that achieve such a result are also suitable and can be used. For example, a dichroic long pass filter used as filter 60 can be utilized to minimize the source light reaching detector 80. According to various embodiments, a non-dichroic long pass filter can be used as filter 60. Filter 60 can also be, for example, a 50/50 beam splitter, 75/25 beam splitter, 25/75 beam splitter. Collimating lenses can be used to minimize the angle and thus the spectral shift of the beam splitter.

According to various embodiments, a filter 60 can be positioned such that the filter is located along an excitation beam path between a light source 10 and a single reaction region 40. According to various other embodiments, a filter 60 can be located between one or more light source 10 and two or more reaction regions 40. According to various embodiments, the filter 60 can be located in an excitation beam path between a condensing lens and a focusing lens (see FIG. 8), a reaction region lens, or a reaction region. According to various other embodiments, the filter 60 can be located in an emission beam path between a reaction region, reaction region lens, or focusing lens and a detector.

A mirror 65 can be located in an excitation beam path between a light source and a reaction region. According to various embodiments, a mirror can be located in an excitation beam path between one or more light source and two or more reaction regions. A mirror can be located between a condensing lens or a filter, and a focusing lens, reaction region lens, or reaction region.

To filter the excitation beams emitted from light source 10, an excitation filter 100 can be disposed between the light source 10 and the filter 60, as shown in FIG. 1. Excitation filter 100 can pass light having the excitation frequency for markers or dyes used in the samples, and can substantially block light having the emission frequency.

An emission filter 120 can be disposed between long pass filter 60 and detector 80. Emission filter 120 can be disposed between filter 60 and detector lens 82 in front of detector 80. The emission filter 120 can pass emission beams having the emission frequency emitted from the illuminated samples and can substantially block light having the excitation frequency.

According to various embodiments, excitation filter 100 and filter 60 together constitute a first system disposed to receive excitation beams 15 and to form excitation beams 25 having the excitation frequency. According to various embodiments, emission filter 120 and filter 60 together constitute a second system disposed to receive emission beams 85 from the focusing lens 35 so as to pass emission beams 85 at the emission frequency to detector 80. Filter 60 can alternatively pass source beams 15 as excitation beams 25 and reflect emission beams 85 to detector 80. According to various embodiments, the excitation and emission filters can be omitted, and the first system can include a filter 60 that reflects or passes excitation beams 25, and the second system can include a filter 60 that passes or reflects, respectively, emission beams 85 to the detector 80.

Figure 2:
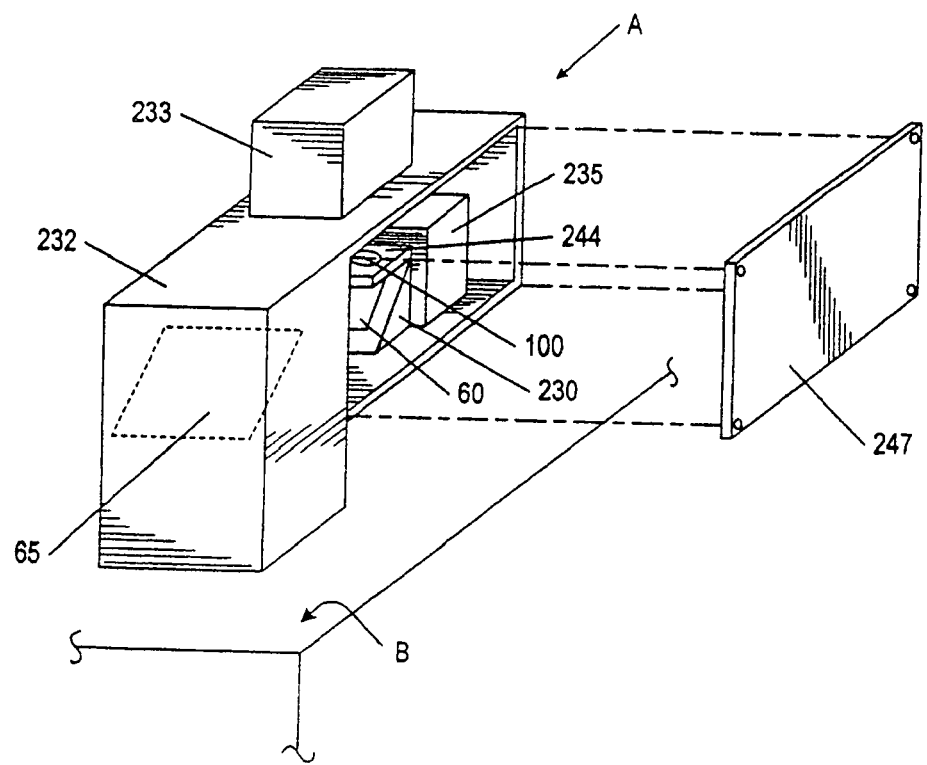
FIG. 2 is a perspective view of an optical instrument for providing the pathway shown in FIG. 1, with a side panel removed.

According to various embodiments, the filter 60, excitation filter 100, and emission filter 120 can be affixed in a module 230 as shown in FIG. 2. These elements can be associated with a selected primary dye used in the samples. The module can be removable from a housing 232 of the instrument A for replacement with another module capable of containing a different filter, excitation filter, and emission filter associated with another selected primary dye. The instrument A can include a light source subhousing 233 and a detector or camera subhousing 235. As shown in FIG. 2, the filter 60 can be located in instrument A such that the filter 60 is at a 45° angle with respect to plane B of the instrument. Other suitable angles of placement of the filter with respect to plane B can be used.

Figure 3:
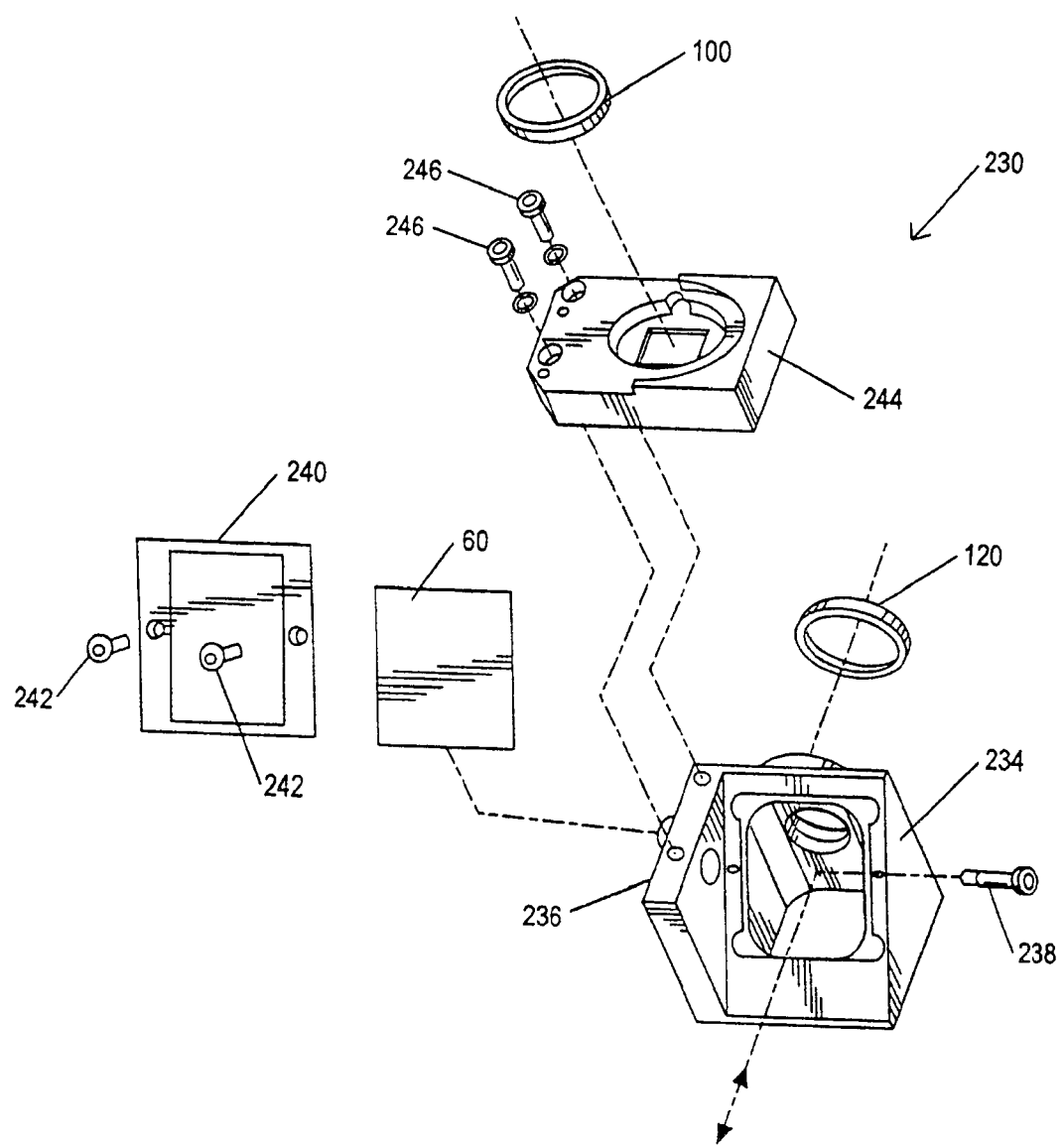
FIG. 3 is an exploded perspective view of the optical instrument shown in FIG. 2.

According to various embodiments and as shown in FIG. 3, the changeable module 230 of an instrument A, as shown in FIG. 2, can include a mounting block 234 including a flange 236 that can be affixed to the housing 232 with a single screw 238. Filter 60 can be held at about 45°, or any other suitable angle, in mounting block 234 with a frame 240 and screws 242. Emission filter 120 can be mounted, for example, with glue, by frictional engagement, snap-fit, or the like, into mounting block 234. Excitation filter 100 can be mounted similarly into mounting member 244, which in turn can be held by screws 246 to mounting block 234. With the module 230 in place, the instrument A can be closed by attaching side plate 247 (FIG. 2), for example, with screws. Optionally, positioning pins (not shown) ensure repeatable alignment. A replacement module can comprise the same mounting block and associated components but with a different long pass filter, excitation filter, and/or emission filter.

Figure 4:
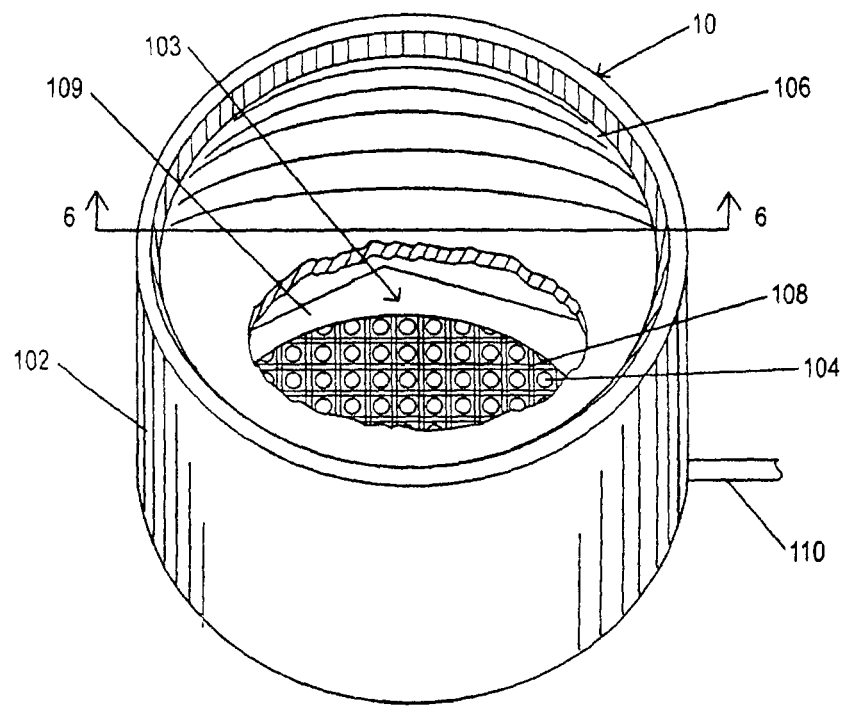
FIG. 4 is a perspective view of an array excitation source used according to various embodiments.
Figure 5:
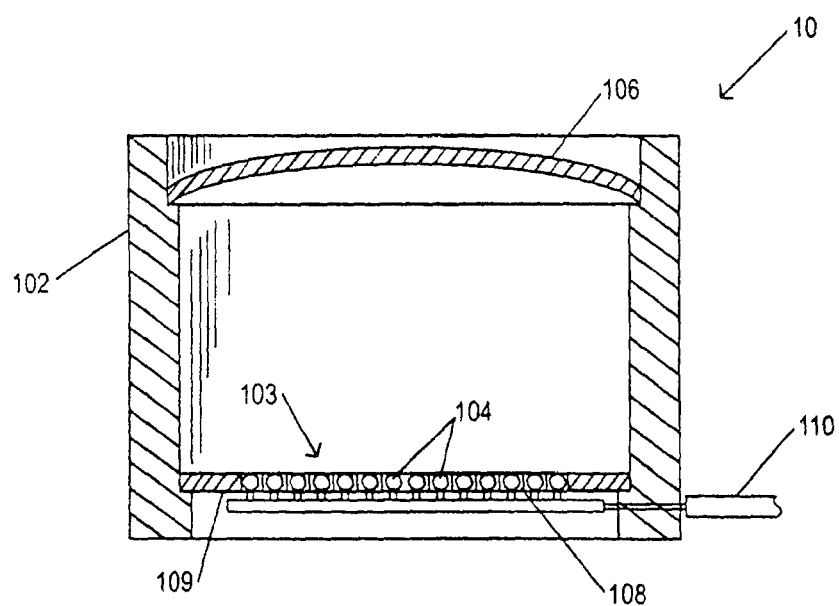
FIG. 5 is a cross-sectional view of the array excitation source shown in FIG. 4 taken along line 5-5 in FIG. 4.

The light source 10 for excitation beams 15 can be an array or bundle of light-sources. According to various embodiments, and as shown in FIGS. 4 and 5, the light source 10 can include an array 103 of individual light sources 104 secured in a substrate 108. The substrate 108 can be made from any material that can withstand the heat emitted from the light source. For example, metal and plastics can be used for substrate 108. The substrate 108 can be mounted into a body 102, as shown. A platform 109 can be provided for mounting the light sources 104 and substrate 108 in the body 102. The array of individual light sources 104 can be secured within body 102 by other suitable devices such as rubber bands, tabs, glue, or other means without the use of substrate 108. The body 102 can include a lens 106, as shown in FIGS. 4 and 5. According to various embodiments, the lens 106 is spaced from array 103 of individual light sources 104. light source 10 can also include power source 110 capable of illuminating each individual light source 104 simultaneously, individually, sequentially, in groups, in rows, or in other configurations or orders of illumination. Groups of individual colors from the array can be sequentially illuminated. The light source can generate excitation beams referred to herein as excitation beams or area light excitation beams.

According to various embodiments, groups of predetermined numbers of light sources 104 can emit respective wavelengths such that the different groups of light sources emit different excitation frequencies. Each group can be arranged as a row of individual light sources 104 or can include a plurality of light sources of a first excitation beam wavelength homogeneously distributed throughout an array along with the light sources of the other excitation beam wavelengths. The wavelength or wavelengths emitted from each group of light sources can correspond to a particular excitation frequency for a marker or dye used in one or more of the samples. A controller, capable of powering one or more of the individual light sources 104 or groups of light sources in the array 103, can power the light sources of a group having a particular wavelength simultaneously or independently of the light sources of the other groups. Each group of light sources powered by the controller can provide excitation beams that illuminate one or more of the plurality of reaction regions simultaneously, and can cause the respective marker or dye to fluoresce.

According to various embodiments, excitation beams emitted from the light source can diverge from the light source at an angle of divergence. The angle of divergence can be, for example, from about 5° to about 75° or more. The angle of divergence can be substantially wide, for example, greater than 45°, yet can be efficiently focused by use of a lens, such as a focusing lens.

As used herein, the terms "excitation source" and "light source" are used interchangeably.

According to various embodiments, the light source can be a Light Emitting Diode (LED). The LED can be, for example, an Organic Light Emitting Diode (OLED), a Thin Film Electroluminescent Device (TFELD), or a Quantum dot based inorganic "organic LED." The LED can include a phosphorescent OLED (PHOLED).

According to various embodiments, a light source can contain one Light Emitting Diode (LED) or an array of LEDs. According to various embodiments, each LED can be a high power LED that can emit greater than or equal to about 1 mW of excitation energy. In various embodiments, a high power LED can emit at least about 5 mW of excitation energy. In various embodiments wherein the LED or array of LEDs can emit, for example, at least about 50 mW of excitation energy, a cooling device such as, but not limited to, a heat sink or fan can be used with the LED. An array of high-powered LEDs can be used that draws, for example, about 10 watts of energy or less, about 10 watts of energy or more. The total power draw can depend on the power of each LED and the number of LEDs in the array. The use of an LED array can result in a significant reduction in power requirement over other light sources, such as, for example, a 75 watt halogen light source or a 150 watt halogen light source. Exemplary LED array sources are available, for example, from Stocker Yale under the trade name LED AREALIGHTS. According to various embodiments, LED light sources can use about 1 microwatt of power or less, for example, about 1 mW, about 5 mW, about 25 mW, about 50 mW, about 1 W, about 5 W, about 50 W, or about 100 W or more, individually or when in used in an array.

According to various embodiments, a quantum dot can be used as a source for luminescence and as a fluorescent marker. The quantum dot based LED can be tuned to emit light in a tighter emission bandpass, thus the quantum dot based LED can increase the efficiency of the fluorescent system. Quantum dots can be molecular-scale optical beacons. The quantum dot nanocrystals can behave like molecular LEDs (light emitting diodes) by "lighting up" biological binding events with a broad palette of applied colors. Quantum dots can provide many more colors than conventional fluorophores. Quantum dots can possess many other very desirable optical properties. Nanocrystal quantum dots can be covalently linked to biomolecules using standard conjugation chemistry. The quantum dot conjugate can then be used to detect a binding partner in a wide range of assays. According to various embodiments, streptavidin can be attached to quantum dots to detect biotinylated molecules in a variety of assays. Quantum dots can also be attached to antibodies and oligonucleotides. Any assay that currently uses, for example, fluorescent-tagged molecules, colorimetric enzymes, or colloidal gold, can be improved with quantum dot nanocrystal-tagged conjugates. An exemplary quantum dot implementation is available from Quantum Dot Corporation of Haywood, Calif. under the trademark QDOT. More information about quantum dots and their applications can be found at, for example, www.qdot.com. U.S. Pat. Nos. 6,207,229, 6,251,303, 6,306,310, 6,319,426, 6,322,901, 6,326,144, 6,426,513, and 6,444,143 to Bawendi et al., U.S. Pat. Nos. 5,990,479, 6,207,392, and 6,423,551 to Weiss et al., U.S. Pat. No. 6,468,808 to Nie et al., and U.S. Pat. No. 6,274,323 to Bruchez et al., describe a variety of biological applications, methods of quantum dot manufacturing, and apparatuses for quantum dot nanocrystals and conjugates, all of which are incorporated herein by reference in their entireties.

Quantum dots can provide a versatile probe that can be used in, for example, in multiplex assays. Fluorescent techniques using quantum dot nanocrystals can be much faster than conventional enzymatic and chemiluminescent techniques, can reduce instrument tie-up, and can improve assay throughput. Colorimetric or detected reflectance techniques can be inferior to fluorescence and difficulties ensue when multiplex assays are developed based on these materials. Quantum dots can absorb all wavelengths "bluer" (i.e., shorter) than the emission wavelength. This capability can simplify the instrumentation required for multiplexed assays, since all different label colors can be excited with a single excitation source.

A Quantum dot based LED can emit light in an emission band that is narrower than an emission band of a normal LED, for example, about 50% narrower or about 25% narrower. The Quantum dot based LED can also emit light at an electrical energy conversion efficiency of about, 90% or more, for example, approaching 100%. OLED films, including Quantum dot based LEDs, can be applied to a thermal block, used for heating and cooling samples, in a fluorescence system without interfering with the operation of the thermal block.

According to various embodiments, when an OLED is used, the OLED can have any of a variety of sizes, shapes, wavelengths, or combinations thereof. The OLED can provide luminescence over a large area, for example, to luminescence multiple sample wells. Scatter or cross-talk light between multiple sample wells for this single OLED can be reduced by either overlaying a mask on the OLED or by patterning the luminescent in the OLED to operatively align with the multiple sample wells. The OLED can be a low power consumption device. Examples of OLEDs in various configurations and wavelengths are described in, for example, U.S. Pat. No. 6,331,438 B1, which is incorporated herein by reference in its entirety. The OLED can include a small-molecule OLED and/or a polymer-based OLED also known as a Light-Emitting Polymer (LEP). A small-molecule OLED that is deposited on a substrate can be used. An OLED that is deposited on a surface by vapor-deposition technique can be used. An OLED can be deposited on a surface by, for example, silk-screening. An LEP can be used that is deposited by, for example, solvent coating.

According to various embodiments, an OLED is used and can be formed from one or more stable, organic materials. The OLED can include one or more carbon-based thin films and the OLED can be capable of emitting light of various colors when a voltage is applied across the one or more carbon-based thin films.

According to various embodiments, the OLED can include a film that is located between two electrodes. The electrodes can be, for example, a transparent anode, a metallic cathode, or combinations thereof. Several separate emission areas can be stimulated between a single set of electrodes where simultaneous illumination of the separate emission areas is required. According to such embodiments, only one power and control module might be required for several apparent light sources. The OLED film can include one or more of a hole-injection layer, a hole-transport layer, an emissive layer, and an electron-transport layer. The OLED can include a film that is about one micrometer in thickness, or less. When an appropriate voltage is applied to the film, the injected positive and negative charges can recombine in the emissive layer to produce light by means of electroluminescence. The amount of light emitted by the OLED can be related to the voltage applied through the electrodes to the thin film of the OLED. Various materials suitable for fabrication of OLEDs are available, for example, from H.W. Sands Corp. of Jupiter, Fla. Various types of OLEDs are described, for example, in U.S. Pat. No. 4,356,429 to Tang, U.S. Pat. No. 5,554,450 to Shi et al., and U.S. Pat. No. 5,593,788 to Shi et al., all of which are incorporated herein by reference in their entireties.

According to various embodiments, an OLED can be used and produced on a flexible substrate, on an optically clear substrate, on a substrate of an unusual shape, or on a combination thereof. Multiple OLEDs can be combined on a substrate, wherein the multiple OLEDs can emit light at different wavelengths. Multiple OLEDs on a single substrate or multiple adjacent substrates can form an interlaced or a non-interlaced pattern of light of various wavelengths. The pattern can correspond to, for example, a sample reservoir arrangement. One or more OLEDs can form a shape surrounding, for example, a sample reservoir, a series of sample reservoirs, an array of a plurality of sample reservoirs, or a sample flow path. The sample path can be, for example, a channel, a capillary, or a micro-capillary. One or more OLEDs can be formed to follow the sample flow path. One or more OLEDs can be formed in the shape of a substrate or a portion of a substrate. For example, the OLED can be curved, circular, oval, rectangular, square, triangular, annular, or any other geometrically regular shape. The OLED can be formed as an irregular geometric shape. The OLED can illuminate one or more sample reservoirs, for example, an OLED can illuminate one, two, three, four, or more sample reservoirs simultaneously, or in sequence. The OLED can be designed, for example, to illuminate all the wells of a corresponding multi-well array.

According to various embodiments, one or more excitation filters can be incorporated into the OLED substrate, thus eliminating additional equipment and reducing the amount of space needed for an optical system. For example, one or more filters can be formed in a layer of a substrate including one or more OLEDs and a layer including a sample flow path. The wavelength emitted by the OLED can be tuned by printing a fluorescent dye in the OLED substrate, as taught, for example, by Hebner et al. in "Local Tuning of Organic Light-Emitting Diode Color by Dye Droplet Application," APPLIED PHYSICS LETTERS, Vol. 73, No. 13 (Sep. 28, 1998), which is incorporated herein by reference in its entirety. When using multiple emission lines in an OLED, the OLED can be used in combination with a multiple bandpass emission filter.

According to various embodiments, an OLED can be substituted in place of any of the systems, devices, or apparatuses where an LED is shown. The OLED light source can have several OLED films stacked and operatively disposed such that several wavelengths of excitation beams can traverse the same optical path to illuminate the sample well. Several OLEDs forming excitation beams of the same wavelength can be stacked to provide higher output to illuminate the sample well.

According to various embodiments, a sample well can be placed in between an excitation source and a detector. The sample well can be a micro card, for example, a microtiter card, such as a 96-well microtiter card. The excitation source can be, for example, an OLED, standard LED, or combination thereof.

According to various embodiments, the light source can be a Solid State Laser (SSL) or a micro-wire laser. The SSL can produce monochromatic, coherent, directional light and can provide a narrow wavelength of excitation energy. The SSL can use a lasing material that is distributed in a solid matrix, in contrast to other lasers that use a gas, dye, or semiconductor for the lasing source material. Examples of solid state lasing materials and corresponding emission wavelengths can include, for example: Ruby at about 694 nm; Nd:Yag at about 1064 nm; Nd:YVO4 at about 1064 nm and/or about 1340 nm and which can be doubled to emit at about 532 nm or about 670 nm; Alexandrite at from about 655 nm to about 815 nm; and Ti:Sapphire at from about 840 nm to about 1100 nm. Micro-wire lasers are lasers where the wavelength of an excitation beam formed by the laser can be tuned or adjusted by altering the size of a wire. Micro-wire lasers are available, for example, from Alabama Laser of Munford, Ala. More information about micro-wire lasers can be found at, for example, www.alspi.com/wirefeeder.pdf. According to various embodiments, other solid state lasers known to those skilled in the art can also be used, for example, laser diodes. The appropriate lasing material can be selected based on the fluorescing dyes used, the excitation wavelength required, or both.

If a SSL is used, the laser can be selected to closely match the excitation wavelength of a fluorescent dye. The operating temperature of the system can be considered in selecting an appropriate SSL. The operating temperature can be regulated or controlled to change the emitted wavelength of the SSL. The light source for the laser can be any source as known to those skilled in the art, such as, for example, a flash lamp. Useful information about various solid state lasers can be found at, for example, www.repairfaq.org/sam/lasersl.htm.

Examples of solid state lasers used in various systems for identification of biological materials can be found in, for example, U.S. Pat. No. 5,863,502 to Southgate et al. and U.S. Pat. No. 6,529,275 B2 to Amirkhanian et al.; both of which are incorporated herein by reference in their entireties.

According to various embodiments, various types of light sources can be used singularly or in combination with other light sources. One or more OLEDs can be used with, for example, one or more non-organic LEDs, one or more solid state lasers, one or more halogen light sources, or combinations thereof.

According to various embodiments, a light source can be used to provide excitation beams to irradiate a sample solution containing one or more dyes. For example, two or more excitation beams having the same or different wavelength emissions can be used such that each excitation beam excites a different respective dye in the sample. The excitation beam can be aimed from the light source directly at the sample, through a wall of a sample container containing the sample, or can be conveyed by various optical systems to the sample. An optical system can include one or more of for example, a mirror, a beam splitter, a fiber optic, a light guide, or combinations thereof.

According to various embodiments, one or more filters, for example, a bandpass filter, can be used with a light source to control the wavelength of an excitation beam. One or more filters can be used to control the wavelength of an emission beam emitted from an excited or other luminescent marker. One or more excitation filters can be associated with a light source to form the excitation beam. One or more filters can be located between the one or more light sources and a sample. One or more emission filters can be associated with an emission beam from an excited dye. One or more filters can be located between the sample and one or more emission beam detectors.

According to various embodiments, one or more filters, for example, a bandpass filter, can be used with a light source to control the wavelength of an excitation beam. One or more filters can be used to control the wavelength of an emission beam emitted from an excited or other luminescent marker. One or more excitation filters can be associated with one or more light sources to form at least one excitation beam. One or more filters can be located between the one or more light sources and a sample. One or more emission filters can be associated with an emission beam from an excited dye. One or more filters can be located between the sample and one or more emission beam detectors.

According to various embodiments, a filter can be a single bandpass filter or a multiple bandpass filter. As used herein, a bandpass filter and a passband filter are used interchangeably. A multiple passband filter can be, for example, a multiple-notch filter or a multi-rugate filter. A multiple passband filter can be used with an incoherent light source, for example, a halogen lamp, a white light source, and/or one or more LEDs or OLEDs emitting light at different wavelengths. A multiple passband filter can be used with a multiple laser-based light source emitting light at different wavelengths. Examples of manufacturing and use of rugate filters and rugate beam splitters can be found in, for example, U.S. Pat. No. 5,863,502 to Southwell, U.S. Pat. No. 6,256,148 to Gasworth, and U.S. Pat. No. 6,529,275 B2 to Rahmlow, Jr., all of which are incorporated herein by reference in their entireties.

According to various embodiments, a multiple passband filter can be used with a dichroic beam splitter, a 50/50 beam splitter, a dichroic beam splitter that has several "passbands," or no beam splitter. A multiple beam splitter can be coated at an angle, causing a variance in a thickness across a filter substrate, to compensate for wavelength shift with an angle. A multiple passband filter can be formed by coating different light interference materials over discrete areas of a substrate used in a multiple passband filter manufacture.

A Rugate filter is an example of an interference coating based on the refractive index that varies continuously in a direction, for example, perpendicular or 45 degrees to the film plane. When the refractive index varies periodically within two extreme values, a minus filter with high transmittance on either side of the rejection band can be made. Periodic Rugate filters can be manufactured.

Rugate notch filters can use refractory metal oxides to achieve coatings with exceptional thermal and environmental stability. These filters can be used in place of other types of notch filters, particularly where durability and reliability are desired. Rugate notch filters are available from Barr Associates (Westford, Mass.). The Rugate notch filter can be used as edge filters and beam splitters. Filter sizes or shapes are not limitations for the rugate notch filter. The rugate notch filter can provide environmental and thermal stability, a broad operating temperature range, narrow rejection bands, variety of shapes & sizes, high throughput, low ripple, and/or a broad spectral range. More information is available from, for example, www.barr-associates-uk.com, www.barrassociates.com/opticalfilters.php.

Multiple-bandpass filters can be made, for example, with a measured blocking of O.D. 6 or better. Notch filters with this type of deep blocking level at the light wavelength can also afford high transmission close to the light line.

According to various embodiments, excitation levels can increase when multiple dyes spaced apart spectrally are irradiated with excitation beams. This can lead to less spectral crosstalk. The dye matrix, condition number, and/or deconvolution in a system can be improved. The increased excitation levels can provide higher signal levels. Higher signal levels can be seen during the utilization of dyes that emit in the "red" spectrum. The dynamic range of the system can be improved. The system can reduce the compensation for variation in the emission beam intensity for various dyes.

According to various embodiments, the multiple dyes can be deposited in a sample well using a fluid transfer technique, such as, for example, manual pipette, robotic pipette, or injection. According to various embodiments, the multiple dyes can be deposited in a sample well, for example, by ink jet spraying, as beads, or as a mixture of a plurality of dyes.

Figure 6A:
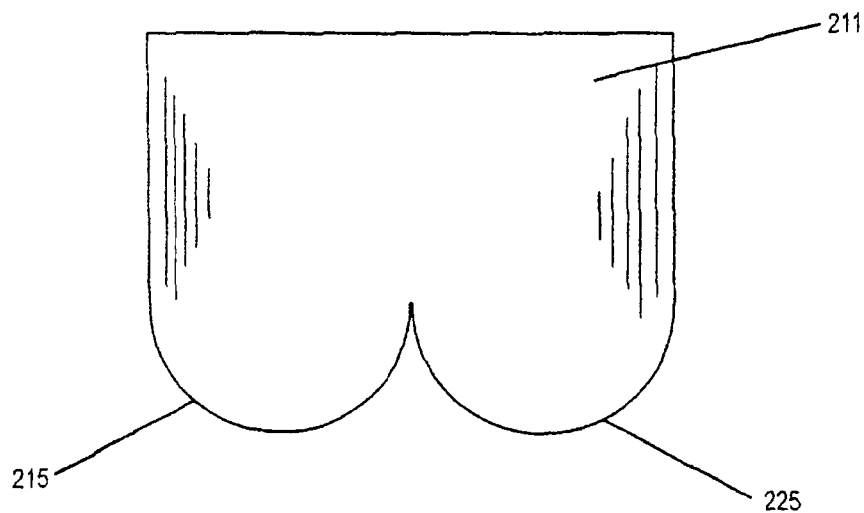
FIGS. 6a and 6b are a side view and an end view, respectively, of an array excitation source, according to various embodiments.
Figure 6B:
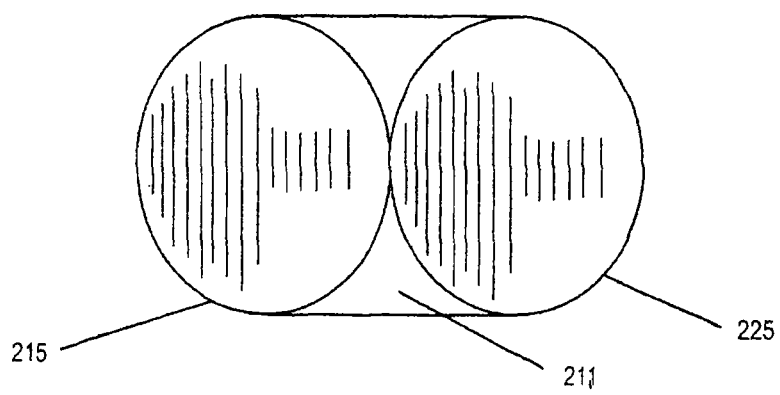

An exemplary light source is shown in FIG. 6a (side view) and FIG. 6b (end view), wherein a single light source array source 211 can include a lens with two focusing areas 215, 225, forming two respective condensed light bundles. The lens can have more than two focusing areas, forming a number of condensed light bundles equal to the number of focusing areas. Each focusing area of the lens can be of any suitable shape, for example, round, oval, elliptical, spherical, semi-spherical, semi-elliptical, or semi-ovoid. The lens can be of unitary construction. According to various embodiments, the lens can be modular, including a base and one or more lens focusing area capable of mounting on the base. According to various embodiments, each lens focusing area can filter the wavelength of the light source. Each lens focusing area can pass a different wavelength of light. According to various embodiments, each lens focusing area can pass the same wavelength of light. Light source array source 211 can comprise an array or bundle of light sources, wherein each light source corresponds to a respective focusing area.

Figure 7A:
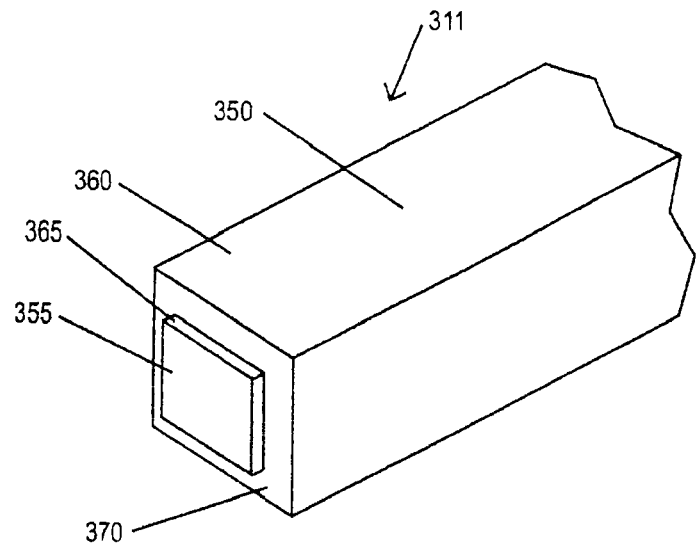
Figure 7B:
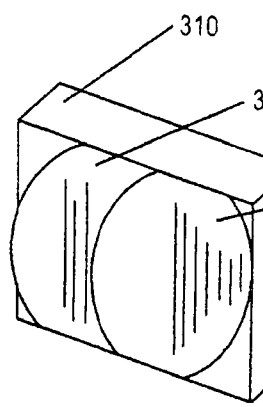
Figure 7C:
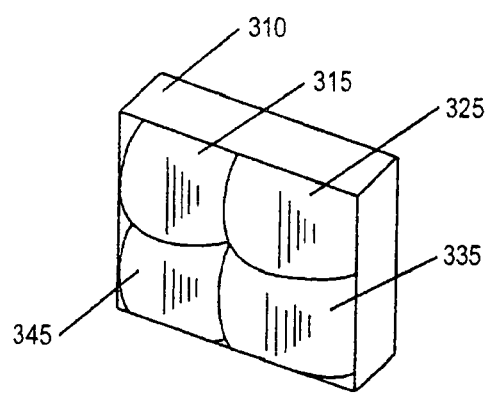

Another exemplary light source, a modular light source, is shown in FIGS. 7a-c. Light source module 311 can receive lens arrays of variable design and quantity. According to various embodiments, a light source module 311 has an outer surface 350 to which any one of a variety of light source lens arrays can be attached. The outer surface 350 can define a square, rectangular, polygonal, circular, oval, or elliptical shape, or any other geometric shape. According to various embodiments, outer surface 350 includes a terminal portion 355 which can extend from a terminal end 360 of the light source module 311. Terminal portion 355 can include a rim 365 which is inset from an edge of the outer surface 350 so as to form a shoulder 370. The terminal portion 355 can be any shape, for example, square, rectangular, polygonal, oval, ellipsoidal, circular, semi-circular, semi-ellipsoidal, semi-ovoid, or any other geometric shape. According to various embodiments, terminal portion 355 can extend from terminal end 360 of light source module 311, as shown in FIG. 7a. According to various embodiments, terminal portion 355 can be a recess in terminal end 360 of light source module 311. Terminal portion 355 can interact with light source lens array 310, various embodiments of which are shown in FIGS. 7b and 7c. According to various embodiments, light source lens array 310 can fit snugly on terminal portion 355 of light source module 311, wherein terminal portion 355 extends from terminal end 360 of light source module 311. According to various embodiments, light source lens array 310 can fit snugly in terminal portion 355 when terminal portion 355 is recessed in terminal end 360 of light source module 311. light source lens array 310 can be removably attached to or fit into terminal portion 355 by friction fit, snap-fit, screwing, or other reversible mounting arrangements. According to various embodiments, light source lens array 310 can be permanently affixed to, mounted on, or fit into terminal portion 355 of light source module 311, such as by, for example, unitary molding, heat welding, adhesive, or other permanent attachment arrangements. Light source lens array 310 can be any shape suitable to interact with terminal portion 355 of light source module 311. According to various embodiments, light source lens array 310 can have a complimentary shape to terminal portion 355. Light source lens array 310 can include one or more light source lens. For example, as shown in FIG. 7b, light source lens array 310 can include light source lens 315 and light source lens 325, which light source lenses can be semi-ovoid. According to various embodiments, light source lens array 310 can include four light source lenses 315, 325, 335, and 345, as shown in FIG. 7c, wherein the light source lenses can be semi-spherical. Each light source lens, such as light source lenses 315, 325, 335, and 345, can be any suitable shape, for example, round, spherical, semi-spherical, spherical, oval, semi-ovoid, elliptical, semi-elliptical, or any other shape capable of focusing light from a light source in light source module 311. The light source lenses can extend above the edge of light source lens array 310 as shown in FIG. 7b, or the light source lenses can be flush with the edge of light source lens array 310 as shown in FIG. 7c. According to various embodiments, each light source lens can form a respective light bundle of a different wavelength from any other light source lens in light source lens array 310. According to various embodiments, each light source lens can emit the same wavelength light bundle. Each light source lens can correspond to a different light source in light source module 311. Each light source lens can be capable of filtering the wavelength of the light source. According to various embodiments including more than one light source lens, the light source lenses can be of unitary construction, or can be formed separately. Light source module 311 can include one or more light generating sources. According to various embodiments, the light-generating source can comprise an array or bundle of light sources.

Figure 8:
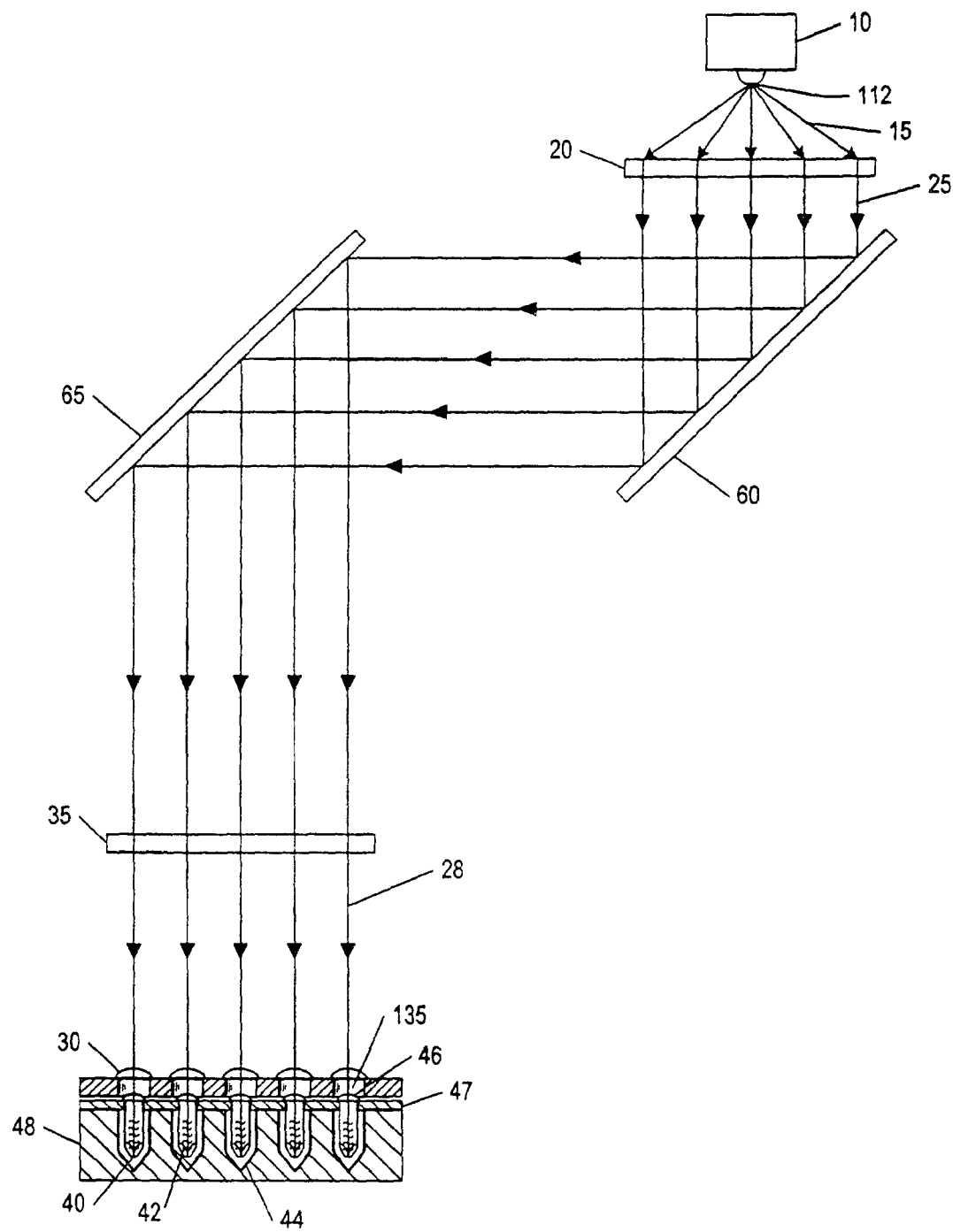
FIG. 8 is a schematic diagram of an optical instrument and an optical pathway generated by the instrument, wherein the instrument includes an array excitation source and a condensing lens, according to various embodiments.

According to various embodiments and as shown in FIG. 8, the light source 10 can comprise a light source 112 and a condensing lens 20, for example, a collimating lens. Excitation beams 15 emitted from the light source 112 diverge from the light source 112 at an angle of divergence. The angle of divergence can be, for example, from about 5° to about 75° or more. The angle of divergence can be substantially wide, for example, greater than 45°, yet can be efficiently focused by the use of a condensing lens 20. According to various embodiments, the condensing lens can be a collimating lens, a Fresnel lens, or a molded glass sphere. According to various embodiments, a condensing lens can receive the excitation light beams 15 from the light source 112 and can form condensed excitation light beams 25, which condensed light beams can be at least partially condensed or bundled, for example, in the form of collimated light beams. According to various embodiments wherein the condensing lens is a collimating lens, light beams originating from a point on the light source that is intersected by the optical axis of the collimating lens can emerge from the collimating lens parallel to the optical axis of the collimating lens. According to various embodiments, the condensing lens can be located one focal length away from the light source. According to various embodiments, the condensing lens can be more than one condensing lens in the form of a condensing lens array. According to various embodiments, there can be one condensing lens provided for each light source. The condensing lens can receive the excitation light beams from a light source and can condense the excitation light beams such that at least one discrete bundle of condensed excitation beams is produced. Each discrete bundle of condensed excitation beams is of the same wavelength but less energy than the initial excitation light beams entering the condensing lens. According to various embodiments wherein the condensing lens is a collimating lens, the collimating lens can form two or more discrete bundles of collimated excitation beams from one light source, for example, four discrete bundles of collimated excitation beams. The condensing lens can be any material known to receive and condense light.

As shown in FIG. 8, condensed excitation beams that have passed through a condensing lens 20, which can be a collimating lens, can be reflected off of long pass filter 60 in a direction toward fold mirror 65. Excitation beams reflected from fold mirror 65 can pass through a focusing lens 35, for example, a Fresnel lens. According to various embodiments, the excitation beams can also be focused by reaction region lenses 30 before illuminating samples 42 in respective reaction regions 40.

Suitable excitation and emission filters for use in optical instruments as described herein can be any conventional optical bandpass filters utilizing, for example, optical interference films, each having a bandpass at a frequency that is optimal for either the excitation wavelength of the fluorescent dye or the emission wavelength of the fluorescent dye. Each filter can have very high attenuation for non-bandpass frequencies to prevent "ghost" images from being reflected and to prevent stray light. For SYBR Green dye, for example, the excitation filter bandpass can center around a 485 nm wavelength, and the emission filter bandpass can center around a 555 nm wavelength. Filter can be tilted so that any reflections do not create ghost images. Filter 60 can transition from reflection to transmission at a wavelength between these two, e.g. about a 510 nm wavelength, so that light of frequencies less than the transition wavelength can be reflected and higher wavelength light can pass through the filter, or vice versa. In this manner, according to various embodiments, filter 60 can function as one or more of an excitation filter and an emission filter.

According to various embodiments, the excitation filter can be replaced by any other emission wavelength excluding device. The emission filter can be replaced by any other excitation wavelength excluding device. The excluding devices can be one or more of a filter, prism, grating, distribution, plate, condensing lens, collimating lens, or mask configured to allow the desired light frequency to pass through, and the undesired light frequency to be blocked, reflected, or diverted. Alternately, the desired light frequency can be reflected or diverted, and the undesired light frequency allowed to pass through the excluding device. An excluding device can be used alone or in combination with one or more of a mirror or lens.

According to various embodiments, the filter 60 can be omitted, and the light source 10 and detector 80 can be located side-by-side so that excitation beams 25 and emission beams 85 are on slightly different optical paths angularly. Light source 10 and detector 80 need not actually be side-by-side if one or more fold mirrors are used. Thus, any such arrangement for achieving the effects described herein should be deemed equivalent. According to exemplary embodiments, when using a filter 60, excitation beams 25 and emission beams 85 will have the same optical paths through Fresnel lens 35.

According to various embodiments, one or more field lens can be used in the optical instrument. The field lens can be a Fresnel lens, or any other suitable lens known to practitioners in the art. According to various embodiments, a first and second field lens can be positioned such that the first field lens can receive excitation beams from the light source array source and pass the excitation beams to the second field lens, which can be located a distance from the first field lens equal to the sum of the focal lengths of the first and second field lenses. The second field lens can pass the excitation beams as a bundle of condensed excitation light beams parallel to the optical axis of the second field lens to a reaction region lens or array, or directly to a plurality of spaced-apart reaction regions. According to various embodiments, a single structure that combines the reaction lens array into the second field lens can be used. According to various embodiments, each bundle of condensed excitation light beams from the second field lens impinges on a respective reaction region lens or reaction region.

According to various embodiments, a pair of field lenses can be used with each light source. According to various other embodiments, a pair of field lenses can be used with multiple light sources. For example, one pair of field lenses can be used for a single line of light sources in a multi-well sample array. According to various embodiments, a field lens pair can be used in combination with one light source, two light sources, or more than two light sources. The use of one pair of field lenses per multiple light sources can reduce the cost of the optical instrument.

According to various embodiments, the sample can contain a fluorescent dye or marker that fluoresces when un-quenched in the presence of the target nucleic acid sequence to which the dye can bind. Fluorescent dye probes can be used. Other dyes that have similar characteristics can be used. The samples can also contain an additional, passive dye that serves as a reference or control.

If a reference dye is included, the dye can include, for example, a nucleic acid sequence labeled with a Rhodamine and/or Fluorescein dye or a derivative thereof. A suitable reference dye is ROX dye available from Applied Biosystems of Foster City, Calif. The passive dye molecule can be selected so as not to take part in a reaction, for example, a PCR reaction, so that fluorescence from the passive dye is substantially without influence from the target nucleic acid sequence and remains constant during the PCR amplification reaction. Fluorescence detected from the passive dye can be used to normalize the fluorescence from the target sequence binding dye by using a standard concentration of the passive dye in one or more of the reaction regions.

The light source 10 can emit excitation beams that include a secondary excitation frequency that causes the passive dye to fluoresce at a secondary emission frequency. The secondary emission frequency can be directed to the detector 80 to generate corresponding secondary data signals. The processor can receive the secondary data signals and compute secondary data representative of the known standard concentration of the passive dye. These data can be used to normalize the primary data, so that the concentration of the target nucleic acid sequence is normalized to the standard concentration of the passive dye after correcting the concentration computations of the target sequence in proportion to adjustments made in exposure time, and in conjunction with normalization for drift, accounted for by analyzing the secondary emission frequency. Greater details about the use of passive dyes and mathematical transformations using data collected from passive dyes are set forth in the *ABI Prism 7000 Sequence Detection System User Guide*, pages A-1 through A-10, available from Applied Biosystems, which is incorporated herein in its entirety be by reference. The secondary excitation frequency can be identical to the primary excitation frequency, and the passive dye can be selected to fluoresce such that the secondary emission frequency can be substantially at the emission frequency of the primary emission beams. In the example of PCR, the primary data signals can be generated during each extension phase of thermal cycling when the target sequence is recombined and the primary dye emission is maximized. The secondary data signals can be generated during each denature phase of thermal cycling when the target sequence is denatured and correspondingly primary dye emission is minimized. Thus, data signals for the primary phase can be substantially representative of the target sequence concentration, and data signals for the secondary phase can be substantially representative of the standard concentration of passive dye.

According to various embodiments, methods are provided whereby excitation beams can impinge on a plurality of spaced apart reaction regions. The excitation beams can cause one or more dye in each of the respective reaction regions to fluoresce, emitting an emission beam. According to various embodiments, the emission beam can pass through a reaction region lens and, optionally, a focusing lens, to impinge upon a filter. According to various embodiments, the emission beam can pass through the filter to a detector, as shown in FIG. 1. According to various other embodiments, the emission beam is reflected off the filter towards a detector. The detector can determine the wavelength of the emission beam as a first data set. The first data set can be sent to a processor 90, as shown in FIG. 1, for determination of the presence or absence of fluorescence in a sample in one or more spaced-apart reaction region. The wavelength and strength of each emission beam can also be detected and recorded in the first data set. According to various embodiments, one or more of the reaction region lens, focusing lens, or filter, can be absent.

According to various embodiments, the detector 80 can be an array detector, for example, a charge injection device (CID), or a charge-coupled device (CCD). A conventional video camera, for example, one containing a CCD detector, can be used. The detector lens 82 and associated electronics for the detector are known to those skilled in the art. An exemplary detector system is the Electrim model 1000L, which can include 751 active pixels horizontally and 242 (non-interlaced) active pixels vertically, and can include a circuit board that directly interfaces to a computer ISA bus. Such cameras can include frame grabber circuitry. Any other digital imaging device or subsystem can be used, or adapted and used, such as CMOS pixels, photodiodes, photomultipliers, or other light receptors. According to various embodiments, the detector can be capable of taking still or freeze-frame images for post processing in a computer.

According to various embodiments, a detector such as a CCD can receive light for a selected integration period and, after analog/digital conversion, can read out digital signal data at a level accumulated over that period. An electronic shutter can effectively control the integration period. Signal data can be generated for each pixel, including those receiving the emission beam from each of the reaction regions A mechanical shutter could be alternately used.

A detector including a multiplicity of photoreceptors (pixels) can be used with a plurality of reaction regions in order to provide separate monitoring of each reaction region. According to various embodiments, a scanning device can be used with a single photodetector, for example, by scanning the fold mirror 65 and using a small aperture detector lens 82 for the detector 80 as shown in FIG. 1. According to various embodiments, a plurality of photomultipliers can be used.

According to various embodiments, a detector lens 82 can be used to focus the emission beam onto detector 80. In another embodiment, a focusing reflector may be substituted for detector lens 82. Such an emission focusing system (detector lens or reflector) can be located after (as shown in FIG. 1) or before filter 60 on either side of emission filter 120, and alternatively can be integrated into a primary focusing system that includes components also used to direct the excitation beams. For example, Fresnel lens 35 can be an objective lens that focuses emission beams 85 onto detector 80.

Detector lens 82 can cooperate with reaction region lens 30 and/or Fresnel lens 35 to focus the individual beams on detector 80. Detector lens 82 can include a large aperture, a low distortion, and minimum vignetting.

According to various embodiments, a single detector 80 can be used to receive the emission beam from multiple reaction regions 40, as shown in FIG. 1, for example. According to various other embodiments, each reaction region can correspond to a single detector. Examples of such detectors can be found, for example, in publication WO 01/69211A1, incorporated herein by reference in its entirety.

According to various embodiments, the processor 90 can be a computer or computer system for determination of the presence or absence and amount of sample components determined by detection of the fluorescence of various fluorescent dyes in the spaced-apart reaction regions. The processor can produce a second data set containing the quantities of various components within each of the pluralities of spaced-apart reaction regions.

According to various embodiments, a method of illuminating multiple spaced-apart reaction regions with a light source can comprise emitting light as an excitation beam from a light source. The excitation beams can impinge on a plurality of spaced-apart reaction regions. A reaction region lens, focusing lens or both, can be set in a path of the excitation beams to focus the excitation beams on a discrete spaced-apart reaction region. A reaction region lens array can be used to focus the excitation beams into separate spaced-apart reaction regions. The excitation beams can impinge upon a respective sample set forth in a respective reaction region. Each sample can react with the excitation beams and can emit emission beams from the sample in the reaction region. The emission beams can pass through the reaction region lens and, according to some embodiments, can impinge on a detector. According to various embodiments, the emission beams having passed through the reaction region lens can pass through a filter before impinging upon a detector. According to various embodiments, the detector can receive the emission beams from a sample in a reaction region and can create a first data set, which can be passed to a processor for determination of the composition of the sample in the reaction region. According to various embodiments, a focusing lens can be used instead of or in combination with a reaction region lens, and can be located between the light source and reaction region.

Figure 9:
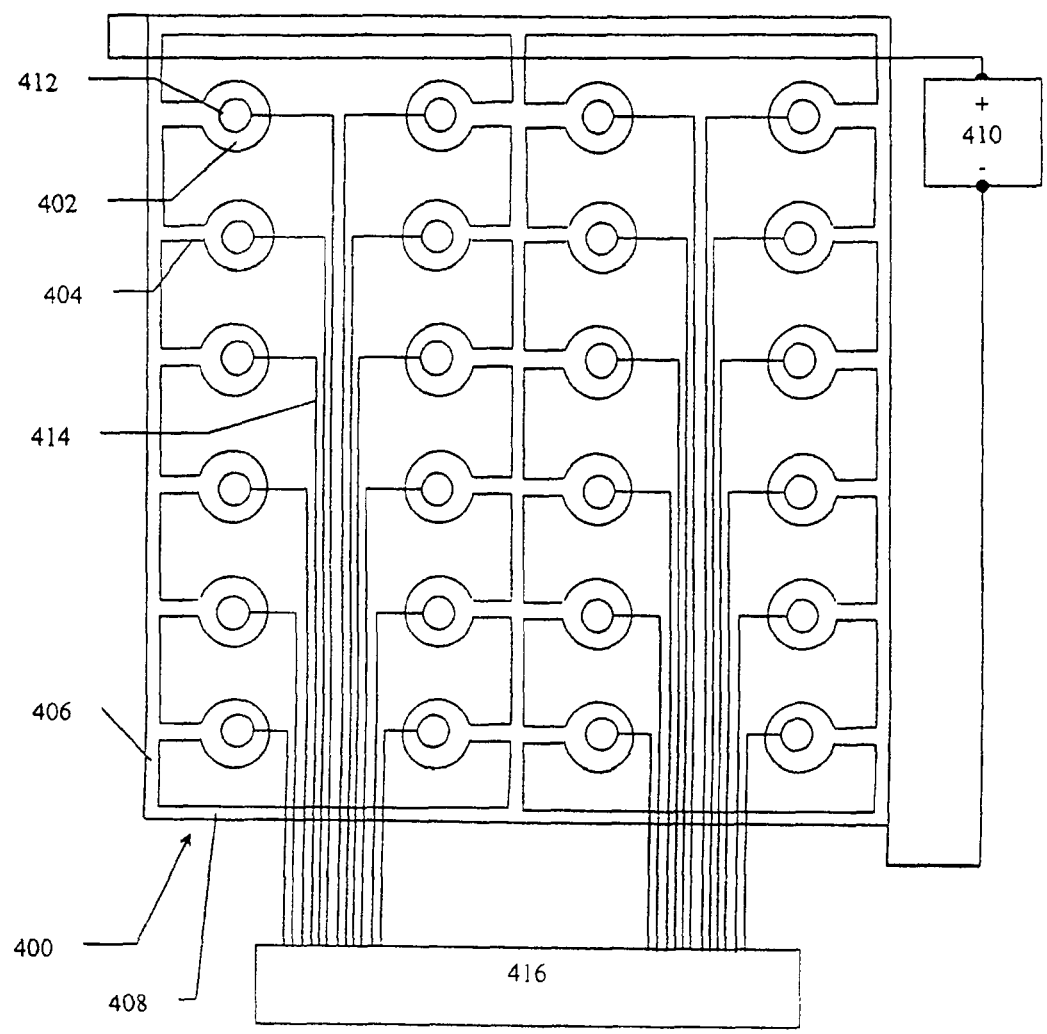
FIG. 9 illustrates an exemplary embodiment of a light source layout, for example, an organic light emitting diode (OLED) layout.

FIG. 9 is a bottom view that illustrates an OLED layout 400 that can be used as a light source, together with a plurality of photodiode detectors 412, according to various embodiments. The OLED layout 400 can include a plurality of OLED well lamps 402, each positioned, when in operation, above a respective well of a multi-well sample well array. Each OLED material well lamp 402 can be connected to, or integrally formed with, a respective connection arm 404 that leads to a layout terminal 406. Each layout terminal can be connected to or integrally formed with the respective connection arms 404 branching from the layout terminal.

The connection arms 404 branch off of side terminals 406 and 408. The OLED layout can be connected to respective opposite electrical connections, for example, opposite terminals of a power supply. The OLED layout can be connected to the power supply through leads arranged at opposite corners of the OLED layout. The power supply can include or be connected to one or more of a switch, a meter, an oscillator, a potentiometer, a detector, a signal processing unit, or the like. Alternatively, or additionally, connection arms 404 can each include a wire or electrical lead in the form of, for example, a metal wire. The OLED layout can include a plurality of individually addressable OLED lighting elements (not shown) with a separate lead connected to each lighting element. The wiring, leads, terminals, connection arms, and the like can be implemented in, for example, a substrate or a film. An OLED layout control unit 410 can be used to supply power and control the OLED layout 400. A plurality of detectors 412 can be electrically connected to a detector control unit 416 through respective detector leads 414 as shown.

The plurality of detectors can be arranged, for example, centered, on the plurality of OLED well lamps 402, on the sides of well lamps that face respective sample wells, and/or when operatively positioned adjacent a multi-well sample well array. The detectors can be configured to detect light emitted from the sample wells of a sample well array, without being flooded or bleached out by the respective OLED well lamps. For example, a mask material can be disposed between the detectors and the respective OLED well lamps. The detector 412 can be formed in the same substrate as the OLED lamp.

The exemplary OLED layout shown in FIG. 9 is shaped to be alignable with a 24 well sample well array. Other embodiments of OLED layouts using various shapes and various numbers of well lamps are within the scope of the present teachings.

According to various embodiments, each well lamp 402 can include, for example, four individual lamps or OLED layers, capable of producing excitation wavelengths at four different frequencies.

The OLED layout can be constructed of a unitary or multi-part construction, of molded material, of stamped material, of screen printed material, of cut material, or the like.

Figure 10:
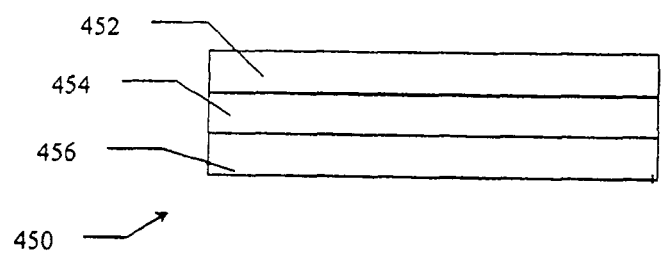
FIG. 10 illustrates an exemplary embodiment of a light source layout, for example, an OLED layout with varying color OLEDs stacked upon each other.

FIG. 10 illustrates an exemplary embodiment of a light source layout. An OLED layout 450 can include varying color OLEDs 452, 454, and 456 stacked upon each other. The layout can be useful for a compact light source design capable of forming excitation beams at varying wavelengths. The OLEDs 452, 454, and 456 can be transparent, allowing excitation beams from each OLED to pass through any other OLED so as to be directed towards a sample. The OLEDs 452, 454, and 456 can emit different colors, same colors, or a combination thereof depending on the color intensity and variety required. The OLEDs 452, 454, and 456 can share an electrode, for example, a cathode. One electrode, for example, an anode, for powering each of the OLEDs 452, 454, and 456 can be connected in electrical isolation from each respective anode to a control unit (not shown) if the capability to independently activate each of the OLEDs 452, 454, and 456 is desired. The OLEDs 452, 454, and 456 can electrically share one electrode, two electrodes, or no electrodes. Any number of OLEDs can be stacked, for example, two OLEDs, three OLEDs, four OLEDs, or more OLEDs, to form a light source, a respective light source, or an array of light sources.

Other embodiments will be apparent to those skilled in the art from consideration of the present specification and practice of the teachings disclosed herein. It is intended that the present specification and examples be considered as exemplary only.

What is claimed is:

1. A method of illuminating a plurality of reaction regions, the method comprising:
   providing a plurality of light emitting diode sources distributed throughout a two-dimensional array;
   providing a plurality of reaction regions comprising a two-dimensional array of spaced-apart reaction regions;
   providing an array detector;
   generating a plurality of excitation beams with the plurality of light emitting diode sources such that plurality of light emitting diode sources illuminate every reaction region of the two-dimensional array of spaced-apart reaction regions;
   directing the excitation beams through a plurality of lenses and into the two-dimensional array of spaced-apart reaction regions;
   generating emission beams from the two-dimensional array of spaced-apart regions; and
   directing the emission beams to the plurality of lenses and a beam splitter and onto the array detector.

2. The method of claim 1, wherein the array detector comprises a charge-coupled device (CCD), charge injection device (CID), a plurality of CMOS pixels, a plurality of photodiodes, or a plurality of photomultipliers.

3. The method of claim 1, further comprising detecting the emission beams transmitted through a Fresnel lens.

4. The method of claim 1, wherein at least one of the plurality of reaction regions includes a sample capable of emitting emission beams when illuminated by the excitation beams, and the method further comprises generating data signals representative of the emission beams.

5. The method of claim 4, wherein the sample comprises components for nucleic acid sequence amplification.

6. A system for illuminating a plurality of reaction regions, the system comprising:
   a block configured to receive a plurality of reaction regions comprising a two-dimensional array of spaced-apart reaction regions retaining a respective sample comprising one or more dyes;
   a plurality of light emitting diodes distributed throughout a two-dimensional array and configured to generate a plurality of excitation beams such that the plurality of light emitting diodes illuminate every reaction region of the two-dimensional array of spaced-apart reaction regions;
   a plurality of lenses configured to direct the excitation beams toward the block and into the two-dimensional array of spaced-apart reaction regions;
   an emission optical system comprising the plurality of lenses, a beam splitter, and an array detector, the emission optical system configured to direct emission beams from the two-dimensional array of spaced-apart reaction regions to the plurality of lenses and the beam splitter and onto the array detector.

7. The system of claim 6, wherein at least some of the plurality of light emitting diodes are distributed throughout a second two dimensional array.

8. The system of claim 6, wherein the array detector comprises a charge-coupled device (CCD), a charge injection device (CID), a plurality of CMOS pixels, a plurality of photodiodes, or a plurality of photomultipliers.

9. The system of claim 6, wherein the emission optical system further comprises a Fresnel lens.

10. The system of claim 6, further comprising a plurality of reaction regions including at least one sample capable of emitting emission beams when illuminated by the excitation beams.

11. The method of claim 10, wherein the sample comprises components for nucleic acid sequence amplification.

12. The system of claim 10, further comprising a thermal cycler configured to thermally cycle the plurality of reaction regions.

13. The system of claim 6, wherein the plurality of light emitting diodes is configured to simultaneously illuminate all of the reaction regions of the two-dimensional array of spaced-apart reaction regions.

14. The system of claim 6, wherein the plurality of reaction regions comprises 96 reaction regions.

15. The system of claim 6, wherein the beam splitter comprises a dichroic beam splitter.

16. The system of claim 6, wherein the beam splitter comprises a 50/50 beam splitter.

17. The system of claim 6, further comprising a first plurality of light emitting diodes characterized by a first excitation wavelength and a second plurality of light emitting diodes characterized by a second excitation wavelength that is different from the first excitation wavelength.

18. The optical instrument of claim 6, further comprising a plurality of reaction regions containing respective samples including one or more dyes.

19. The optical instrument of claim 18, wherein the samples include ingredients for a polymerase chain reaction.

20. The system of claim 6, wherein the first plurality of light emitting diodes is distributed throughout a first array and the second plurality of light emitting diodes is distributed throughout a second array.

21. The optical instrument of claim 6, further comprising a thermal controller for controlling a temperature of the block.

22. A system for illuminating a plurality of reaction regions, the system comprising:
   a region configured to receive a plurality of reaction regions comprising a two-dimensional array of spaced-apart reaction regions containing respective samples;

a two-dimensional array of light sources configured to generate a plurality of excitation beams such that the two-dimensional array of light sources illuminate every reaction region of the two-dimensional array of spaced-apart reaction regions;

a plurality of lenses configured to direct the excitation beams toward the two-dimensional array of spaced-apart reaction regions;

an emission optical system comprising the plurality of lenses, a beam splitter, and an array detector, the emission optical system configured to direct emission beams from the two-dimensional array of spaced-apart reaction regions to the plurality of lenses and the beam splitter and onto the array detector.

23. The optical instrument of claim 22, wherein the two-dimensional array of light sources comprises a two-dimensional array of light emitting diodes.

24. The optical instrument of claim 22, further comprising a plurality of reaction regions containing respective samples including one or more dyes.

25. The optical instrument of claim 24, wherein the samples include ingredients for a polymerase chain reaction.

26. A system for illuminating a plurality of reaction regions, the system comprising:
a block configured to receive a plurality of reaction regions comprising a two-dimensional array of spaced-apart reaction regions;
a plurality of light emitting diodes distributed throughout a two-dimensional array and configured to generate a plurality of excitation beams disposed along a plurality of excitation optical paths such that the plurality of light emitting diodes illuminate the two-dimensional array of spaced-apart reaction regions;
an array detector configured to receive a plurality of emission beams disposed along a plurality of emission optical paths from the two-dimensional array of spaced-apart reaction regions;
an optical system comprising an optical element and configured to direct the plurality of excitation beams toward the block and into the two-dimensional array of spaced-apart reaction regions;
wherein the optical system is configured such that each excitation optical path overlaps a respective one of the emission optical paths between the two-dimensional array of spaced-apart reaction regions and the optical element;
wherein the optical element is disposed at a location along the plurality of excitation optical paths that is between the light emitting diodes and the two-dimensional array of spaced-apart reaction regions, and the optical element is disposed at a location along the emission optical paths so as to receive the plurality of emission beams from the two-dimensional array of spaced-apart reaction regions; and
wherein the optical element comprises a beam splitter.

27. The system of claim 26, wherein the array detector comprises a plurality of photodiodes.

28. A system for illuminating a plurality of reaction regions, the system comprising:
a block configured to receive a plurality of reaction regions comprising a two-dimensional array of spaced-apart reaction regions;
a plurality of light emitting diodes distributed throughout a two-dimensional array and configured to generate a plurality of excitation beams disposed along a plurality of excitation optical paths such that the plurality of light emitting diodes illuminate the two-dimensional array of spaced-apart reaction regions;
an array detector configured to receive a plurality of emission beams disposed along a plurality of emission optical paths from the two-dimensional array of spaced-apart reaction regions;
an optical system comprising an optical element and configured to direct the plurality of excitation beams toward the block and into the two-dimensional array of spaced-apart reaction regions;
wherein the optical system is configured such that each excitation optical path overlaps a respective one of the emission optical paths between the two-dimensional array of spaced-apart reaction regions and the optical element;
wherein the optical element is disposed at a location along the plurality of excitation optical paths that is between the light emitting diodes and the two-dimensional array of spaced-apart reaction regions, and the optical element is disposed at a location along the emission optical paths so as to receive the plurality of emission beams from the two-dimensional array of spaced-apart reaction regions; and
wherein the system comprises a plurality of modules, each module including a beam splitter, an excitation filter, and an emission filter, the beam splitters being configured to pass the excitation beams and reflect the emission beams, the optical element comprising the beam splitters.

29. The system of claim 28, wherein the array detector comprises a plurality of photodiodes.

* * * * *